United States Patent [19]

Eicken et al.

[11] Patent Number: 4,844,733
[45] Date of Patent: Jul. 4, 1989

[54] HERBICIDAL N-ARYLTETRAHYDROPHTHALIMIDE DERIVATIVES

[75] Inventors: Karl Eicken, Wachenheim; Peter Plath, Frankenthal; Bruno Wuerzer, Otterstadt; Norbert Meyer, Ladenburg, all of Fed. Rep. of Germany

[73] Assignee: BASF Aktiengesellschaft, Ludwigshafen, Fed. Rep. of Germany

[21] Appl. No.: 22,140

[22] Filed: Mar. 5, 1987

[30] Foreign Application Priority Data

Mar. 6, 1986 [DE] Fed. Rep. of Germany ....... 3607300

[51] Int. Cl.$^4$ .................... A01N 37/32; C07D 209/48
[52] U.S. Cl. .......................................... 71/96; 548/513
[58] Field of Search .......................... 548/513; 71/96

[56] References Cited

U.S. PATENT DOCUMENTS

| B. 211,786 | 1/1975 | Haddock et al. ............. 71/98 X |
| 3,483,246 | 12/1969 | Kaufman ..................... 71/96 X |
| 4,260,555 | 4/1981 | Myatt ......................... 71/105 X |

FOREIGN PATENT DOCUMENTS

| 0006152 | 1/1980 | European Pat. Off. |
| 0207894 | 1/1987 | European Pat. Off. |
| 2071100 | 9/1981 | United Kingdom. |
| 2150929 | 7/1985 | United Kingdom. |

OTHER PUBLICATIONS

Patent Abstracts of Japan (1985) 9(317): (C19)(240) Abstracts No. 60-152465.
Okada et al., Chemical Abstracts, vol. 103: 215163m (1985).

*Primary Examiner*—Donald G. Daus
*Assistant Examiner*—Diana G. Rivers
*Attorney, Agent, or Firm*—Keil & Weinkauf

[57] ABSTRACT

N-aryltetrahydrophthalimide derivatives and intermediates therefor of the general formula I

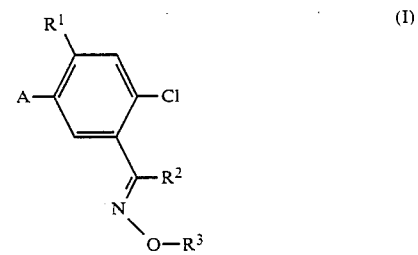

where
A is $O_2N-$, $H_2N-$ or

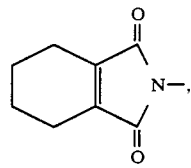

corresponding to compounds Ia, Ib and Ic,
$R^1$ is hydrogen, fluorine or chlorine,
$R^2$ is hydrogen or cyano,
$R^3$ is $C_1-C_6$-alkyl, $C_2-C_6$-alkenyl or $C_2-C_6$-alkynyl, which each may be substituted by halogen or $C_1-C_4$-alkoxy, or is $C_1-C_3$-alkyl, which may be substituted by $C_3-C_8$-alkenyl, $C_3-C_8$-alkynyloxycarbonyl or $C_2-C_{10}$-alkoxycarbonyl which may be substituted in the alkoxy moiety by $C_1-C_4$-alkoxy, halogen or phenyl,
and herbicides which contain compounds of the formula Ic.

5 Claims, No Drawings

HERBICIDAL N-ARYLTETRAHYDROPHTHALIMIDE DERIVATIVES

The present invention relates to novel N-aryltetrahydrophthalimide derivatives and intermediates therefor of the general formula I

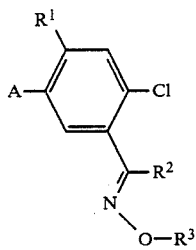

where
A is $O_2N-$, $H_2N-$ or

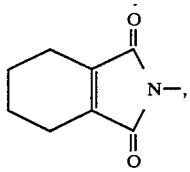

corresponding to compounds Ia, Ib and Ic,
$R^1$ is hydrogen, fluorine or chlorine,
$R^2$ is hydrogen or cyano,
$R^3$ is $C_1$–$C_6$-alkyl, $C_2$–$C_6$-alkenyl or $C_2$–$C_6$-alkynyl, which each may be substituted by halogen or $C_1$–$C_4$-alkoxy, or is $C_1$–$C_3$-alkyl, which may be substituted by $C_3$–$C_8$-alkenyl, $C_3$–$C_8$-alkynyloxycarbonyl or $C_2$–$C_{10}$-alkoxycarbonyl which may be substituted in the alkoxy moiety by $C_1$–$C_4$-alkoxy, halogen or phenyl.

The present invention also relates to the use of the N-aryltetrahydrophthalimide derivatives Ic as herbicides and to herbicides which contain compounds of the formula Ic.

GB-A-2,150,929 discloses N-aryltetrahydrophthalimides of type I′

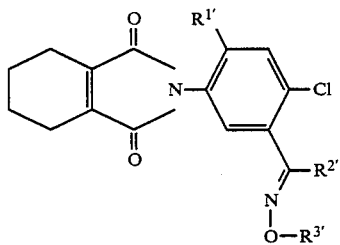

where
$R^{1'}$ is hydrogen, halogen or pseudohalogen,
$R^{2'}$ and $R^{3'}$ are each independently hydrogen, alkyl, alkaryl, araryl, aryl, alkoxyalkyl, alkoxycarbonylalkyl or haloalkyl.

These compounds have been recommended for use as herbicides, but in particular at low application rates they leave something to be desired.

It is an object of the present invention to develop new N-aryltetrahydrophthalimide derivatives Ic of improved herbicidal action for the same or a reduced application rate.

We have found that this object is achieved with a novel N-aryltetrahydrophthalimide derivative Ic defined above. We have also found that a compound Ic is highly suitable for use as a herbicide.

Characteristic of the general herbicidal action of compounds Ic is the 3,4,5,6-tetrahydrophthalimide group.

The oxime ether moiety

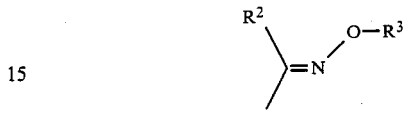

has a favorable effect in respect of enhanced action and selectivity of the herbicide.

Compounds Ia are obtainable by the following methods:

(a) For the case where $R^2$ is hydrogen: The nitrobenzene oxime compounds of the formula Ia can be prepared in similar manner to known processes by reacting the nitroformyl compound IIa either with hydroxylamine hydrochloride in the presence of acid-binding agents to give an oxime IIa′ and subsequently reacting the latter with a compound $R^3$-Br, or directly with an O-substituted hydroxylamine $H_2NO$-$R^3$ or a salt thereof in the presence or absence of an acid-binding agent.

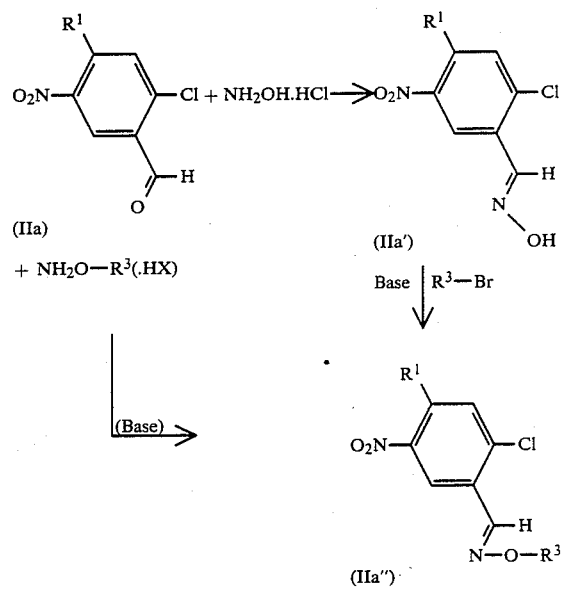

(b) For the case where $R^2$ is cyano: The nitrobenzene oxime compounds Ia are obtained by reacting m-nitrobenzyl cyanide IIa‴ with an alkyl nitrite $R^4ONO$, where $R^4$ is $C_1$–$C_8$-alkyl, in the presence of a sodium alcoholate at from 0° C. to room temperature to give the sodium salt of the oximinonitrile of the formula IIa$^{IV}$ and subsequently reacting the latter with a compound $R^3$-Br at room temperature in an aprotic dipolar solvent such as acetonitrile. In one version, the nitro compound IIa$^V$ is obtained by reacting an o-chlorobenzyl cyanide IIa$^{VI}$ with an alkyl nitrite $R^4ONO$ in the abovementioned manner to give the sodium salt of the oximinonitrile IIa$^{VI}$, then reacting the latter with a compound R$^3$-Br in an aprotic dipolar solvent and finally reacting the product with nitrating acid at from −10° to +50° C., preferably at from 0° to 25° C.

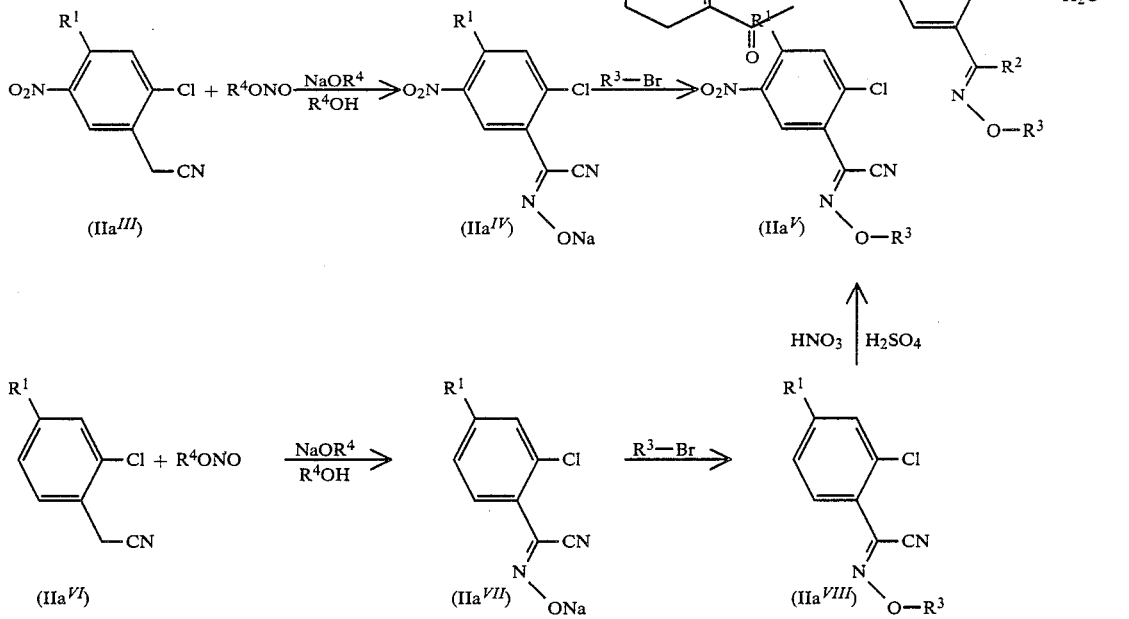

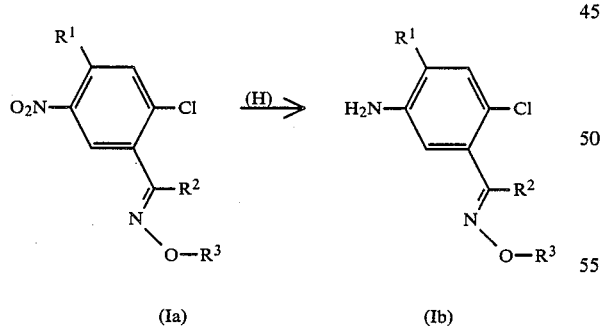

Compounds Ib are obtainable by the following methods:

The aniline oxime derivative Ib is prepared in a conventional manner by reducing the nitro compound Ia, either by reducing with the salt of divalent tin or iron in an aqueous acidic alcoholic medium, for example HCl/water/ethanol, or by partial catalytic hydrogenation by means of a noble metal catalyst, for example platinum or palladium, at from 0° to 50° C.

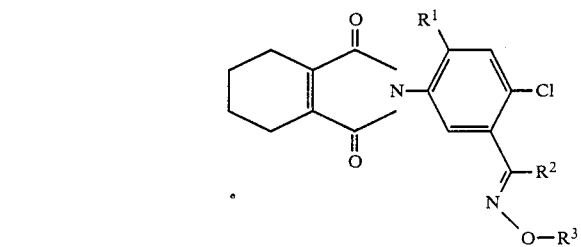

Compounds Ic are obtainable by the following methods:

The N-aryltetrahydrophthalimide Ic is obtainable from 3,4,5,6-tetrahydrophthalic anhydride and an aniline oxime derivative in the presence or absence of a solvent at from 60° to 200° C. Suitable solvents are lower carboxylic acids, such as glacial acetic acid or propionic acid or aprotic solvents. On working in an aprotic solvent, it is advisable to employ a water separator to remove the water of reaction azeotropically.

Of compounds Ic, preference is given to those where R$^1$ is hydrogen or chlorine. R$^2$ is preferably hydrogen. Preferred radicals R$^3$ are C$_1$-C$_4$-alkyl, in particular methyl, ethyl or n-propyl,
C$_2$-C$_4$-alkenyl, in particular vinyl or allyl,
C$_2$-C$_4$-alkynyl, in particular ethynyl,
C$_1$-C$_4$-haloalkyl, in particular trifluoromethyl or trichloromethyl,
C$_1$-C$_2$-alkyl, which is substituted by C$_2$-C$_9$-alkoxycarbonyl, in particular methoxycarbonylmethyl, ethoxycarbonylmethyl, methoxycarbonyleth-1-yl, ethoxycarbonyleth-1-yl, n-propoxycarbonyleth-1-yl, n-butoxycarbonylmethyl, n-hexoxycarbonylmethyl, n-butoxycarbonyleth-1-yl, n-pentoxycarbonyleth-1-yl, n-octyloxycarbonyleth-1-yl or (2-ethyl-n-hexyloxy)carbonyleth-1-yl,
C$_1$-C$_2$-alkyl which is substituted by C$_3$-C$_6$-alkenyloxycarbonyl, in particular allyloxycarbonylmethyl or allyloxycarbonyleth-1-yl, $C_1$–$C_2$-alkyl which is substituted by $C_3$–$C_6$-alkynyloxycarbonyl, in particular ethynyloxycarbonyleth-1-yl, $C_1$–$C_2$-alkyl which is substituted by $C_2$–$C_6$-alkoxycarbonyl which is substituted in the alkoxy moiety by $C_1$–$C_4$-alkoxy, in particular methoxymethoxycarbonylmethyl, methoxymethoxycarbonyleth-1-yl, ethoxymethoxycarbonylethyl and ethoxymethoxycarbonyleth-1-yl, $C_1$–$C_2$-alkyl which is substituted by $C_2$–$C_6$-alkoxycarbonyl which is substituted in the alkoxy moiety by phenyl, in particular benzyloxycarbonylmethyl and benzyloxycarbonyleth-1-yl.

When $R^2$ is hydrogen, $R^3$ is particularly preferably methyl, ethyl, n-propyl, methoxycarbonylmethyl, ethoxycarbonylmethyl, or methoxycarbonyleth-, ethoxycarbonyleth-, n-propyloxycarbonyleth- or allyloxycarbonyleth-1-yl. When $R^2$ is cyano, $R^3$ is particularly preferably methyl, allyl, methoxycarbonylmethyl, ethoxycarbonylmethyl or methoxycarbonyleth-1-yl.

Examples of suitable compounds are 3,4,5,6-tetrahydrophthalimides having the following substituents on the imide nitrogen:

3-(methoxyiminomethyl)-4-chlorophenyl
3-(ethoxyiminomethyl)-4-chlorophenyl
3-(n-propyliminomethyl)-4-chlorophenyl
3-(allyliminomethyl)-4-chlorophenyl
3-(methoxyethoxyiminomethyl)-4-chlorophenyl
3-(propargyloxyiminomethyl)-4-chlorophenyl
3-(methoxycarbonylmethoxyiminomethyl)-4-chlorophenyl
3-(ethoxycarbonylmethoxyiminomethyl)-4-chlorophenyl
3-(n-propoxycarbonylmethoxyiminomethyl)-4-chlorophenyl
3-(n-butoxycarbonylmethoxyiminomethyl)-4-chlorophenyl
3-(tert.-butoxycarbonylmethoxyiminomethyl)-4-chlorophenyl
3-(n-hexoxycarbonylmethoxyiminomethyl)-4-chlorophenyl
3-(methoxycarbonylmethylmethoxyiminomethyl)-4-chlorophenyl
3-(ethoxycarbonylmethylmethoxyiminomethyl)-4-chlorophenyl
3-(n-propoxycarbonylmethylmethoxyiminomethyl)-4-chlorophenyl
3-(isopropoxycarbonylmethylmethoxyiminomethyl)-4-chlorophenyl
3-(n-butoxycarbonylmethylmethoxyiminomethyl)-4-chlorophenyl
3-(allyloxycarbonylmethylmethoxyiminomethyl)-4-chlorophenyl
3-(isobutoxycarbonylmethylmethoxyiminomethyl)-4-chlorophenyl
3-(tert.-butoxycarbonylmethylmethoxyiminomethyl)-4-chlorophenyl
3-(n-pentoxycarbonylmethylmethoxyiminomethyl)-4-chlorophenyl
3-(n-octyloxycarbonylmethylmethoxyiminomethyl)-4-chlorophenyl
3-(propargyloxycarbonylmethylmethoxyiminomethyl)-4-chlorophenyl
3-(methoxycarbonylethylmethoxyiminomethyl)-4-chlorophenyl
3-(ethoxycarbonylethylmethoxyiminomethyl)-4-chlorophenyl
3-(methoxycarbonyldimethylmethoxyiminomethyl)-4-chlorophenyl
3-(ethoxycarbonyldimethylmethoxyiminomethyl)-4-chlorophenyl
5-(methoxyiminomethyl)-2,4-dichlorophenyl
5-(ethoxyiminomethyl)-2,4-dichlorophenyl
5-(n-propoxyiminomethyl)-2,4-dichlorophenyl
5-(allyloxyiminomethyl)-2,4-dichlorophenyl
5-(ethoxycarbonylmethoxyiminomethyl)-2,4-dichlorophenyl
5-(n-butoxycarbonylmethoxyiminomethyl)-2,4-dichlorophenyl
5-(n-propoxycarbonylmethylmethoxyiminomethyl)-2,4-dichlorophenyl
5-(ethoxycarbonylmethoxyiminomethyl)-4-chloro-2-fluorophenyl
5-(n-butoxycarbonylmethoxyiminomethyl)-4-chloro-2-fluorophenyl
5-(n-propoxycarbonylmethylmethoxyiminomethyl)-4-chloro-2-fluorophenyl
3-(methoxyiminoacetonitrile)-4-chlorophenyl
3-(ethoxyiminoacetonitrile)-4-chlorophenyl
3-(allyloxyiminoacetonitrile)-4-chlorophenyl
3-(methoxycarbonylmethoxyiminoacetonitrile)-4-chlorophenyl
3-(ethoxycarbonylmethoxyiminoacetonitrile)-4-chlorophenyl
3-(n-propoxycarbonylmethoxyiminoacetonitrile)-4-chlorophenyl
3-(methoxycarbonylmethylmethoxyiminoacetonitrile)-4-chlorophenyl
3-(ethoxycarbonylmethylmethoxyiminoacetonitrile)-4-chlorophenyl
3-(n-propoxycarbonylmethyl(methoxyiminoacetonitrile)-4-chlorophenyl
5-(methoxyiminoacetonitrile)-2,4-dichlorophenyl
5-(allyloxyiminoacetonitrile)-2,4-dichlorophenyl
5-(methoxycarbonylmethoxyiminoacetonitrile)-2,4-dichlorophenyl
5-(ethoxycarbonylmethoxyiminoacetonitrile)-2,4-dichlorophenyl
5-(methoxycarbonylmethylmethoxyiminoacetonitrile)-2,4-dichlorophenyl
5-(ethoxycarbonylmethylmethoxyiminoacetonitrile)-2,4-dichlorophenyl
5-(n-propoxycarbonylmethylmethoxyiminoacetonitrile)-2,4-dichlorophenyl The N-aryltetrahydrophthalimides Ic, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, and paraffin, tetrahydrocarbons such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methyl-pyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenol-sulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols and octadecanols, salts of sulfated fatty alcohol glycol ethers, condensation products of sulfonated naphthalene and naphthalene derivatives with formaldehyde, condensation products of naphthalene or naphthalenesulfonic acids with phenol or formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate and ureas, and vegetable products such as grain flours, bark meal, wood meal and nutshell meal, cellulosic powders, etc.

The formulations contain from 0.1 to 95, and preferably from 0.5 to 90, % by weight of active ingredient.

The active ingredients, or agents containing them, may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of year, the plants to be combated and their growth stage, and varies from 0.01 to 5.0, and preferably from 0.03 to 0.5, kg/ha.

In view of the number of weeds that can be combated, the tolerance of the active ingredients by crop plants, and the desired influence on their growth, and in view of the numerous application methods possible, the compounds according to the invention may—depending on their substitution pattern—be used in a large number of crop plants.

The following crops may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rapeseed |
| *Brassica napus* var. *napobrassica* | swedes |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |
| *Coffea arabica (Coffea canephora, Coffea liberica)* | coffee plants |
| *Cucumis melo* | melons |
| *Cucumis sativus* | cucumbers |
| *Cynodon dactylon* | Bermudagrass |
| *Daucus carota* | carrots |
| *Elais guineensis* | oil palms |
| *Fragaria vesca* | strawberries |
| *Glycine max* | soybeans |
| *Gossypium hirsutum (Gossypium arboreum Gossypium herbaceum, Gossypium vitifolium)* | cotton |
| *Helianthus annuus* | sunflowers |
| *Helianthus tuberosus* | Jerusalem artichoke |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum (N. rustica)* | tobacco |
| *Olea europaea* | olive trees |
| *Oryza sativa* | rice |
| *Phaseolus lunatus* | limabeans |
| *Phaseolus mungo* | mungbeans |
| *Phaseolus vulgaris* | snapbeans, greenbeans, dry beans |
| *Pennisetum glaucum* | pearl millet |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor (s. vulgare)* | sorghum |
| *Sorghum dochna* | sorgo |

| Botanical name | Common name |
| --- | --- |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the N-aryltetrahydrophthalimide derivatives of the general formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, other ureas, diphenyl ethers, triazinones, uracils, benzofuran derivatives, cyclohexane-1,3-dione derivatives, etc.

The novel N-aryltetrahydrophthalimide derivatives Ic may be applied on their own or together with other herbicides and/or crop protection agents. Examples of these are agents for combating pests or phytopathogenic fungi or bacteria. It is also possible to prepare mixtures with mineral salt solutions and with non-phytotoxic oils and oil concentrates.

EXAMPLES

Manufacture of N-substituted aryltetrahydrophthalimide derivatives Ic

EXAMPLES 1 TO 4

At 20° C., 230 mmoles of O-methylenehydroxylamine hydrochloride was added to a solution of 150 mmoles of a 2-chloro-5-nitrobenzaldehyde derivative in 150 ml of methylene chloride. Subsequently, 240 mmoles of triethylamine in 20 ml of methylene chloride was dripped in. The mixture was then stirred for 15 hours at room temperature and worked up in the usual manner.

A solution of 92 mmoles of the product in 400 ml of ethyl acetate was hydrogenated in the presence of 2 g of 10% Pd/carbon (10 wt%) at 17° to 20° C. while stirring, and worked up in the usual manner.

100 mmoles of the product obtained in this manner and 105 mmoles of 3,4,5,6-tetrahydrophthalic anhydride were heated for 8 hours in 180 ml of glacial acetic acid and worked up in the usual manner.

The results are given in Table 1.

TABLE 1

| Compound No. | $R^1$ | $R^2$ | $R^3$ | Mp. [°C.] |
| --- | --- | --- | --- | --- |
| Compounds Ia ($A = O_2N-$) | | | | |
| 1a | H | H | $CH_3$ | 98–99 |
| 2a | H | H | $C_2H_5$ | 56–57 |
| 3a | H | H | $n-C_3H_7$ | 37–38 |
| 4a | Cl | H | $CH_3$ | 68–70 |
| Compounds Ib ($A = H_2N-$) | | | | |
| 1b | H | H | $CH_3$ | 47–49 |
| 2b | H | H | $C_2H_5$ | 48–54 |
| 3b | H | H | $n-C_3H_7$ | oil |
| 4b | Cl | H | $CH_3$ | viscous mass |
| Compounds Ic | | | | |
| (A = 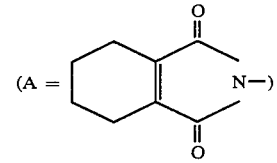) | | | | |
| 1c | H | H | $CH_3$ | 139–41 |
| 2c | H | H | $C_2H_5$ | 97–98 |
| 3c | H | H | $n-C_3H_7$ | 86–87 |
| 4c | Cl | H | $CH_3$ | 143–145 |

EXAMPLES 5 TO 21

At room temperature and while stirring, 200 mmoles of powdered potassium carbonate was introduced in 4 portions into a solution of 100 mmoles of a 2-chloro-5-nitrobenzaldehydeoxime derivative and 110 mmoles of bromocarboxylic acid ester in 140 ml of dry dimethylformamide, and the mixture was stirred for 15 hours at room temperature. The mixture was then stirred into 600 ml of cold water and subjected to suction filtration, and the residue was worked up in the usual manner.

65 ml of concentrated hydrochloric acid was added to a solution of the product in 270 ml of ethanol, and 490 mmoles of tin(II) chloride dihydrate was introduced over a period of 30 minutes while stirring; the mixture was subsequently stirred for 1 hour at 60° C. The ethanol was evaporated under reduced pressure, and the residue was introduced into a mixture of 155 ml of 50 wt% aqueous NaOH and 400 ml of ice water in such a manner that the temperature did not exceed +5° C. The mixture was worked up in the usual manner.

79 mmoles of this product and 87 mmoles of 3,4,5,6-tetrahydrophthalic anhydride were stirred in 150 ml of glacial acetic acid for 1 hour at 50° C. and refluxed for 7 hours. After the mixture had cooled, it was worked up in the usual manner.

The results are shown in Table 2.

TABLE 2

| Compound No. | $R^1$ | $R^2$ | $R^3$ | Mp. [°C.] |
| --- | --- | --- | --- | --- |
| Compounds Ia ($A = O_2N-$) | | | | |
| 5a | H | H | $CH_2CO_2CH_3$ | 106–107 |
| 6a | H | H | $CH_2CO_2C_2H_5$ | 71–72 |
| 7a | H | H | $CH(CH_3)CO_2CH_3$ | 89–90 |
| 8a | H | H | $CH(CH_3)CO_2C_2H_5$ | 65–67 |
| 9a | H | H | $CH(CH_3)CO_2-n-C_3H_7$ | 73–75 |
| 10a | H | H | $CH(CH_3)CO_2CH_2-CH=CH_2$ | 73–74 |
| 11a | H | H | $CH_2-CO_2-n-C_4H_9$ | oil |
| 12a | H | H | $CH_2-CO_2-n-C_6H_{13}$ | 64–65 |

TABLE 2-continued

| Compound No. | R¹ | R² | R³ | Mp. [°C.] |
|---|---|---|---|---|
| 13a | H | H | $CH_2-CO_2-CH_2-CH=CH_2$ | 65-67 |
| 14a | H | H | $CH(CH_3)CO_2-n-C_4H_9$ | oil |
| 15a | H | H | $CH(CH_3)CO_2-n-C_5H_{11}$ | oil |
| 16a | H | H | $CH(CH_3)CO_2-n-C_8H_{17}$ | oil |
| 17a | H | H | $CH(CH_3)CO_2-CH_2CH(C_2H_5)n-C_4H_9$ | oil |
| 18a | H | H | $CH(CH_3)CO_2-C\equiv CH$ | 110-111 |
| 19a | H | H | $CH(CH_3)CO_2-CH_2-\text{C}_6\text{H}_5$ | 68-72 |
| 20a | H | H | $CH(CH_3)CO_2(CH_3)OCH_3$ | 40-45 |
| 21a | H | H | $CH(CH_3)CO_2(CH_2)_2OC_2H_5$ | 61-62 |

Compounds Ib
($A = H_2N-$)

| Compound No. | R¹ | R² | R³ | Mp. [°C.] |
|---|---|---|---|---|
| 5b | H | H | $CH_2CO_2CH_3$ | oil |
| 6b | H | H | $CH_2CO_2C_2H_5$ | 34-36 |
| 7b | H | H | $CH(CH_3)CO_2CH_3$ | oil |
| 8b | H | H | $CH(CH_3)CO_2C_2H_5$ | viscous mass |
| 9b | H | H | $CH(CH_3)CO_2-n-C_3H_7$ | viscous mass |
| 10b | H | H | $CH(CH_3)CO_2CH_2-CH=CH_2$ | viscous mass |
| 11b | H | H | $CH_2-CO_2-n-C_4H_9$ | oil |
| 12b | H | H | $CH_2-CO_2-n-C_6H_{13}$ | oil |
| 13b | H | H | $CH_2-CO_2-CH_2-CH=CH_2$ | oil |
| 14b | H | H | $CH(CH_3)CO_2-n-C_4H_9$ | oil |
| 15b | H | H | $CH(CH_3)CO_2-n-C_5H_{11}$ | oil |
| 16b | H | H | $CH(CH_3)CO_2-n-C_8H_{17}$ | oil |
| 17b | H | H | $CH(CH_3)CO_2-CH_2CH(C_2H_5)-n-C_4H_9$ | oil |
| 18b | H | H | $CH(CH_3)CO_2-C\equiv CH$ | oil |
| 19b | H | H | $CH(CH_3)CO_2-CH_2-\text{C}_6\text{H}_5$ | oil |
| 20b | H | H | $CH(CH_3)CO_2(CH_2)_2OCH_3$ | oil |
| 21b | H | H | $CH(CH_3)CO_2(CH_2)_2OC_2H_5$ | oil |

Compounds Ic

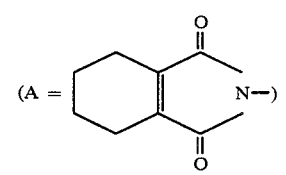

| Compound No. | R¹ | R² | R³ | Mp. [°C.] |
|---|---|---|---|---|
| 5c | H | H | $CH_2CO_2CH_3$ | oil |
| 6c | H | H | $CH_2CO_2C_2H_5$ | 116-117 |
| 7c | H | H | $CH(CH_3)CO_2CH_3$ | viscous mass |
| 8c | H | H | $CH(CH_3)CO_2C_2H_5$ | 85-87 |
| 9c | H | H | $CH(CH_3)CO_2-n-C_3H_7$ | viscous mass |
| 10c | H | H | $CH(CH_3)CO_2CH_2-CH=CH_2$ | viscous mass |
| 11c | H | H | $CH_2-CO_2-n-C_4H_9$ | 91-92 |
| 12c | H | H | $CH_2-CO_2-n-C_6H_{13}$ | 64-66 |
| 13c | H | H | $CH_2-CO_2-CH_2-CH=CH_2$ | 83-86 |
| 14c | H | H | $CH(CH_3)CO_2-n-C_4H_9$ | oil |
| 15c | H | H | $CH(CH_3)CO_2-n-C_5H_{11}$ | oil |
| 16c | H | H | $CH(CH_3)CO_2-n-C_8H_{17}$ | oil |
| 17c | H | H | $CH(CH_3)CO_2-CH_2CH(C_2H_5)-n-C_4H_9$ | oil |
| 18c | H | H | $CH(CH_3)CO_2-C\equiv CH$ | oil |
| 19c | H | H | $CH(CH_3)CO_2-CH_2-\text{C}_6\text{H}_5$ | oil |
| 20c | H | H | $CH(CH_3)CO_2(CH_2)_2OCH_3$ | oil |
| 21c | H | H | $CH(CH_3)CO_2(CH_2)_2OC_2H_5$ | oil |

EXAMPLES 22 TO 29

560 mmoles of a 2-chlorobenzylcyanide derivative was introduced into a solution of 560 mmoles of 30% strength sodium methylate in 200 ml of ethanol. At +10° C. and while stirring, 280 mmoles of neopentyl glycol dinitrite was dripped in over a period of 30 minutes, and stirring was continued for a further 30 minutes at 25° C. at +5° C., 200 ml of methyl tert-butyl ether was dripped in and the mixture was then worked up in the usual manner.

At room temperature, 160 mmoles of a bromide $R^3$-Br was dripped into a solution of 150 mmoles of this sodium salt in 150 ml of dry dimethyl-formamide. After the mixture has been stirred for 24 hours it was worked up in the usual manner.

At +5° C., 110 mmoles of this reaction mixture was dripped, while stirring, into a mixture of 12 ml of 100% strength $HNO_3$ (d=1.51) and 100 ml of concentrated $H_2SO_4$; the mixture was stirred for 2 hours at +5° C. The reaction mixture was poured onto 500 g of ice and worked up in the usual manner.

Similarly to Examples 5 to 10, the corresponding aniline was obtained as an oil from 41 mmoles of this nitro compound in 120 ml of methanol and 26 ml of concentrated hydrochloric acid by reduction with 36 g of tin(II) chloride dihydrate.

32 mmoles of the aniline obtained and 35 mmoles of 3,4,5,6-tetrahydrophthalic anhydride in 100 ml of glacial acetic acid were reacted similarly to Examples 5 to 10. The compound obtained was purified by chromatography using silica gel and a 9:1 mixture of toluene and ethyl acetate.

The results are given in Table 3.

TABLE 3

| Compound No. | $R^1$ | $R^2$ | $R^3$ | Mp. [°C.] |
|---|---|---|---|---|
| Compounds Ia ($A = O_2N-$) | | | | |
| 22a | H | CN | $CH_2-CH=CH_2$ | 73–75 |
| 23a | H | CN | $CH_2-CO_2CH_3$ | 105–107 |
| 24a | H | CN | $CH_2-CO_2C_2H_5$ | 104–105 |
| 25a | H | CN | $CH(CH_3)CO_2CH_3$ | oil |
| 26a | Cl | CN | $CH_3$ | 78–81 |
| 27a | Cl | CN | $CH_2-CO_2CH_3$ | 107–109 |
| 28a | Cl | CN | $CH_2-CO_2C_2H_5$ | 109 |
| 29a | Cl | CN | $CH(CH_3)CO_2CH_3$ | 111–113 |
| Compounds Ib ($A = H_2N-$) | | | | |
| 22b | H | CN | $CH_2-CH=CH_2$ | oil |
| 23b | H | CN | $CH_2-CO_2CH_3$ | oil |
| 24b | H | CN | $CH_2-CO_2C_2H_5$ | oil |
| 25b | H | CN | $CH(CH_3)CO_2CH_3$ | viscous mass |
| 26b | Cl | CN | $CH_3$ | 88–91 |
| 27b | Cl | CN | $CH_2-CO_2CH_3$ | 95–98 |
| 28b | Cl | CN | $CH_2-CO_2C_2H_5$ | 79–82 |
| 29b | Cl | CN | $CH(CH_3)CO_2CH_3$ | oil |
| Compounds Ic | | | | |

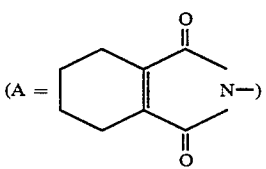

| 22c | H | CN | $CH_2-CH=CH_2$ | oil |
|---|---|---|---|---|
| 23c | H | CN | $CH_2-CO_2CH_3$ | viscous mass |
| 24c | H | CN | $CH_2-CO_2C_2H_5$ | viscous mass |
| 25c | H | CN | $CH(CH_3)CO_2CH_3$ | viscous mass |
| 26c | Cl | CN | $CH_3$ | oil |
| 27c | Cl | CN | $CH_2-CO_2CH_3$ | 108–110 |
| 28c | Cl | CN | $CH_2-CO_2C_2H_5$ | oil |
| 29c | Cl | CN | $CH(CH_3)CO_2CH_3$ | 135–138 |

USE EXAMPLES

The herbicidal action of the N-aryltetrahydrophthalimide derivatives of the general formula Ic on the growth of test plants was illustrated by the following greenhouse experiments.

The vessels employed were plastic flowerpots having a volume of 300 $cm^3$, and which were filled with a sandy loam containing about 3.0% humus. The seeds of the test plants were sown shallow, and separately, according to species.

For the preemergence treatment, the active ingredients were applied to the surface of the soil immediately after the seeds had been sown. The compounds were emulsified or suspended in water as vehicle, and sprayed through finely distributing nozzles. The application rate was 3.0 kg/ha. After the agents had been applied, the vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, the test plants were grown to a height of from 3 to 15 cm, depending on growth form, before being treated. For this treatment, either plants which had been sown directly in the pots and grown there were selected, or plants which had been grown from seedlings and transplanted to the vessels a few days before treatment. The application rates for postemergence treatment varied from ingredient to ingredient and were from 0.03 to 0.06 kg/ha. No covers were placed on the vessels in this treatment method.

The pots were set up in the greenhouse—species from warmer areas at from 20° to 36° C., and species from moderate climates at 10° to 20° C. The experiments were run for 2 to 4 weeks. During this period the plants were tended and their reactions to the various treatments assessed.

The plants used for the greenhouse experiments were *Abutilon theophrasti, Amaranthus retroflexus, Arachis hypogaea, Avena sativa, Chenopodium album, chrysanthemum coronarium, Echinochloa crus-galli, Galium aparine*, Ipomoea spp., *Lamium amplexicaule, Lolium multiflorum, Mercurialis annua, Polygonum aviculare, Solanum nigrum, Stellaria media*, and *Triticum aestivum*.

On preemergence application, compounds nos. 1c and 2c (applied at a rate of 3 kg/ha) proved to be suitable for combating monocotyledonous weeds. Oats, for example, were hardly affected, if at all.

Postemergence, compounds nos. 3c and 4c proved to have a strong herbicidal action on dicotyledonous unwanted plants at a rate of 0.06 kg/ha. They also proved selective in groundnuts, which suffered no appreciable damage.

Compound 9c, at a rate of 0.03 kg/ha, proved to be suitable for combating a broad spectrum of unwanted plants; wheat, as an example of a crop plant, suffered hardly any damage. This compound is therefore a selective herbicidal active ingredient.

By comparison with prior art active ingredient A from GB-A-2,150,929 compound no. 5c exhibited a considerably stronger herbicidal action on a number of unwanted plants.

We claim:

1. An N-aryltetrahydrophthalimide of the formula

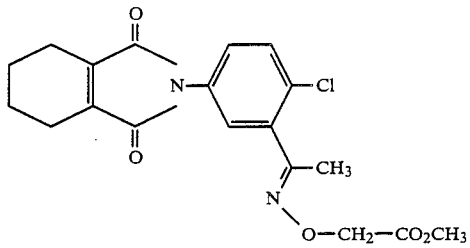

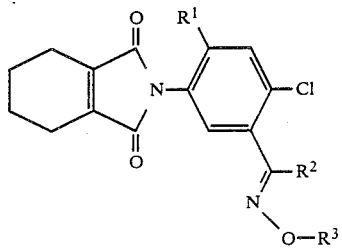

where $R^1$ and $R^2$ are each hydrogen and $R^3$ and $C_1$–$C_3$-alkyl which is substituted by $C_3$–$C_8$-alkenyloxycarbonyl, by $C_3$–$C_8$-alkynyloxycarbonyl or by $C_2$–$C_{10}$-alkoxycarbonyl, which may be substituted in the alkoxy moiety by $C_1$–$C_4$-alkoxy, halogen or phenyl.

2. A compound of the formula Ic as defined in claim 1, wherein $R^3$ is $CH(CH_3)CO_2CH_3$.

3. A compound of the formula Ic as defined in claim 1, wherein $R^3$ is $CH_2CO_2CH_3$.

4. A herbicidal composition which comprises: a carrier and/or diluent and an effective amount of a compound of the formula Ic as defined in claim 1.

5. A process for controlling the growth of unwanted plants which comprises: applying to the unwanted plants or their habitat a herbicidally effective amount of a compound Ic as defined in claim 1.

* * * * *